United States Patent [19]

Mori et al.

[11] Patent Number: 5,698,591

[45] Date of Patent: Dec. 16, 1997

[54] TRIFLUOROMETHANESULFINANILIDE, PROCESS FOR PREPARING TRIFLUOROMETHANESULFONANILIDE FROM THE SAME, AND A CONTROLLING AGENT FORMULATED FROM TRIFLUOROMETHANESULFINANILIDE

[75] Inventors: Tatsuya Mori; Yoji Takada, both of Osaka, Japan

[73] Assignee: Sumitomo Chemical Company, Limited, Osaka, Japan

[21] Appl. No.: 760,799

[22] Filed: Dec. 5, 1996

[30] Foreign Application Priority Data

Dec. 7, 1995 [JP] Japan ................. 7-318850
Jul. 5, 1996 [JP] Japan ................. 8-176266
Sep. 10, 1996 [JP] Japan ................. 8-239592

[51] Int. Cl.$^6$ .............. A01N 37/44; C07C 313/06; C07C 303/36
[52] U.S. Cl. .............................. 514/535; 560/12
[58] Field of Search ................. 514/535; 560/12

[56] References Cited

U.S. PATENT DOCUMENTS 4,403,994 9/1983 Hignett .

FOREIGN PATENT DOCUMENTS

| 2015793 | 11/1990 | Canada . |
| 0 027 693 | 4/1981 | European Pat. Off. . |
| 57-156407 | 9/1982 | Japan . |
| 3-56455 | 3/1991 | Japan . |

OTHER PUBLICATIONS

Chemical Abstracts, "Trifluoromethanesulfonanilides as insectidies", vol. 98, No. 9, 67132, 28 Feb. 1983.

Konrad V. Werner, Journal of Fluorine Chemistry, "Perfluoroalkylsulfinamides by Addition of F–Alkyl Grignard Reagents to N–Sulfinimines", vol. 8, No. 5, 1976, pp. 451–455.

P. Brougham et al., Synthesis, "Oxidation Reaction Using Magnesium Monoperphthalate: A Comparison with m–Chloroperoxybenzoic Acid", No. 11, 1987, pp. 1015–1017.

J. Chem. Soc., Perkin Trans. 1, "Same Studies on Peptide Analogues Involving the Sulphinamide Group", pp. 2169–2176 (1991).

Synthesis, "Oxidation Reactions Using Magnesium Monoperphthalate: A Comparison with m–Chloroperoxybenzoic Acid", pp. 1015–1017 (1987).

Primary Examiner—Michael G. Ambrose
Attorney, Agent, or Firm—Cushman Darby & Cushman IP Group of Pillsbury Madison & Sutro, LLP

[57] ABSTRACT

A trifluoromethanesulfinanilide compound having a structure represented by the following formula:

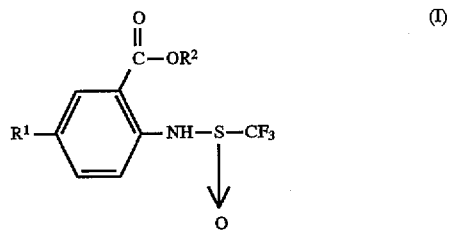

wherein $R^1$ represents a halogen and $R^2$ represents a lower alkyl group is provided. In addition, a process is provided for oxidizing the trifluoromethanesulfinanilide compound with a magnesium monoperoxydicarboxylate to prepare a trifluoromethanesulfonanilide having a structure represented by the following formula:

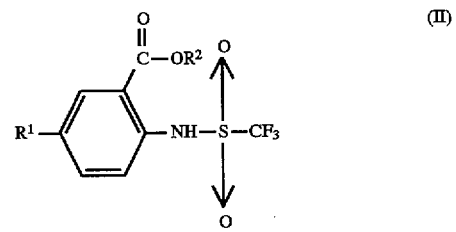

The trifluoromethanesulfinanilide compound (I) also serves as an excellent active ingredient of a controlling agent for regulating the population of house dust mites.

18 Claims, No Drawings

TRIFLUOROMETHANESULFINANILIDE, PROCESS FOR PREPARING TRIFLUOROMETHANESULFONANILIDE FROM THE SAME, AND A CONTROLLING AGENT FORMULATED FROM TRIFLUOROMETHANESULFINANILIDE

BACKGROUND OF THE INVENTION

1. Field of Invention

The present invention relates to a trifluoromethanesulfinanilide, a process for preparing trifluoromethanesulfonanilide from the same, and a controlling agent containing trifluoromethanesulfinanilide as an active ingredient, the controlling agent being suitable for such applications as regulating the population of house dust mites.

2. Description of Related Art

Trifluoromethanesulfonanilides, which have been discussed in Japanese Patent Kokai (Laid Open) No. 57-156407, the complete disclosure of which is incorporated herein by reference, are generally represented by following formula (II):

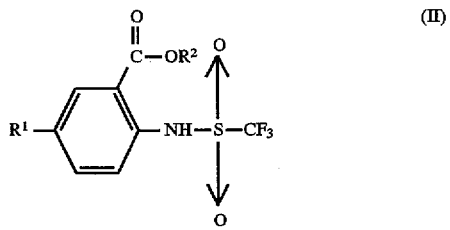

wherein:

$R^1$ represents a halogen, such as a chlorine, bromine, or iodine atom; and $R^2$ represents a lower alkyl group.

As referred to herein, lower alkyl groups include alkyl groups having one to four carbon atoms, such as, without limitation, a methyl, ethyl, propyl, or butyl group. Preferably, the lower alky group is a methyl or ethyl group.

Trifluoromethanesulfonanilides are known to be suitable for application as active ingredients of insecticides and acaricides.

SUMMARY OF THE INVENTION

It is an object of the present invention to provide a compound that can advantageously be employed in the preparation of trifluoromethanesulfonanilides.

In accordance with the principals of the present invention, this object is obtained by providing a trifluoromethanesulfinanilide, which is represented by the following formula (I):

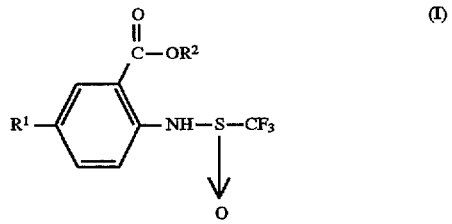

wherein:

$R^1$ represents a halogen, such as a chlorine, bromine, or iodine atom; and $R^2$ represents a lower alkyl group.

Another object of the present invention is to provide a process for preparing trifluoromethanesulfonanilides by employing a trifluoromethanesulfinanilide having a structure represented by formula (I). In accordance with the principals of the present invention, this object is obtained by providing a process of oxidizing a trifluoromethanesulfinanilide compound having a structure represented by formula (I) with a magnesium monoperoxydicarboxylate to convert the trifluoromethanesulfinanilide to a trifluoromethanesulfonanilide having the structure represented by formula (II).

It is still another object of the present invention to provide a method of preparing a trifluoromethanesulfinanilide compound having a structure represented by formula (I). In accordance with the principals of the present invention, this object is obtained, for example, by reacting an aniline compound with a trifluoromethanesulfinyl chloride and/or trifluoromethanesulfinic anhydride in the presence of a base, or by reacting an aniline compound with sodium trifluoromethanesulfinate in the presence of an amine salt and thionyl chloride or phosgene, or by oxidizing a trifluoromethanesulfenanilide compound with a peroxidated compound.

The trifluoromethanesulfinanilide compound of the present invention is suitable for use as an active ingredient of a controlling agent for regulating the population of house dust mites.

These and other objects, features, and advantages of the present invention will become apparent from the following detailed description which discusses, by way of example, the principles of the present invention.

DESCRIPTION OF THE PREFERRED EMBODIMENTS

A detailed description of the present invention is provided below.

A trifluoromethanesulfinanilide compound having a structure consistent with the aforementioned formula (I) can be prepared, by way of example and without limitation on the present invention, by reacting an aniline compound with trifluoromethanesulfinyl chloride and/or trifluoromethanesulfinic anhydride in the presence of a base. The aniline compound is represented by the following formula (III):

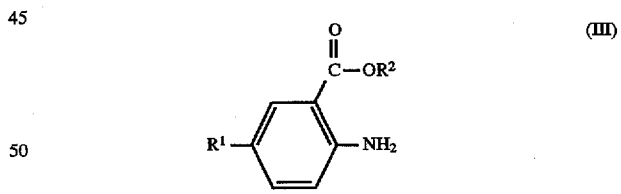

wherein:

$R^1$ represents a halogen; and $R^2$ represents a lower alkyl group.

The trifluoromethanesulfinyl chloride generally has the molecular formula $CF_3S(O)Cl$. The trifluoromethanesulfinic anhydride generally has the molecular formula $(CF_3S(O))_2O$. Each of these compounds can be prepared, for instance, in accordance with the process described in Chem. Ber. 107, 508 (1974), the complete disclosure of which is incorporated herein by reference.

The preparation of the trifluoromethanesulfinanilide via this reaction is usually conducted in a solvent. Exemplary solvents include, without limitation, the following: aliphatic hydrocarbons, such as n-hexane, n-heptane, and the like; alicyclic hydrocarbons, such as cyclohexane and the like;

aromatic hydrocarbons, such as toluene, xylene, benzene, and the like; halogenated hydrocarbons, such as methylene chloride, chloroform, carbon tetrachloride, 1,2-dichloroethane, chlorobenzene, and the like; ethers, such as diisopropyl ether, tetrahydrofuran, dioxane, and the like; and any combination thereof.

Exemplary bases include, without limitation, the following: organic bases, such as pyridine, triethylamine, N,N-diethylaniline, N,N-dimethylaniline, and the like; alkali metal hydroxides, such as sodium hydroxide, potassium hydroxide, and the like; alkali metal carbonates, such as sodium carbonate, potassium carbonate, and the like; and any combination thereof.

The reaction temperature for carrying out this reaction can be, for example, within a range from about −20° C. to about the boiling temperature of the selected solvent, or from about −20° C. to about 100° C.

The molar ratio of, one the one hand aniline and trifluoromethanesulfinyl chloride and/or trifluoromethanesulfinic anhydride, and on the other hand the selected base, is not limited and can be adjusted in accordance with routine experimentation. However, this ratio can advantageously be set to be equimolar or substantially equimolar.

Subsequent to completion of the reaction between the aniline and the trifluoromethanesulfinyl chloride and/or trifluoromethanesulfinic anhydride, the reaction solution can be subjected to conventional post-treatment procedures, such as extraction with organic solvent, concentration and the like to isolate the trifluoromethanesulfinanilide compound. The trifluoromethanesulfinanilide then can be further purified by one or more conventional operations, such as recrystallization, chromatography, and the like.

The compound having a structure consistent with the aforementioned formula (I) also can be prepared by reacting an aniline compound having a structure consistent with formula (III) with sodium trifluoromethanesulfinate in the presence of an amine salt and thionyl chloride or phosgene. Sodium trifluoromethanesulfinate generally has the molecular formula $CF_3S(O)ONa$, and can be prepared by the process described in Japanese Patent Kokai No. 3-56455, the complete disclosure of which is incorporated herein by reference.

This reaction also can be performed in a solvent. Exemplary solvents for this reaction include, without limitation, the following: aliphatic hydrocarbons, such as n-hexane, n-heptane, and the like; alicyclic hydrocarbons, such as cyclohexane and the like; aromatic hydrocarbons, such as toluene, xylene, benzene, and the like; halogenated hydrocarbons, such as methylene chloride, chloroform, carbon tetrachloride, 1,2-dichloroethane, chlorobenzene, and the like; and any combination thereof.

Exemplary amine salts include, without limitation, hydrochlorides, p-toluene sulfonates and methane sulfonates of pyridine, triethylamine, N,N-diethylaniline, dimethylamine, and the like.

The reaction temperature for carrying out this reaction can be, for example, within a range from about −20° C. to about the boiling temperature of the selected solvent, or from about −20° C. to about 100° C.

The molar ratio of, one the one hand aniline and sodium trifluoromethanesulfinate, and on the other hand the selected base, is not limited and can be adjusted in accordance with routine experimentation. However, this ratio can advantageously be set to be equimolar or substantially equimolar.

Subsequent to completion of the reaction between the aniline and the sodium trifluoromethanesulfinate, the reaction solution can be subjected to conventional post-treatment procedures, such as extraction with organic solvent, concentration and the like to isolate the resulting trifluoromethanesulfinanilide compound. This compound then can be further purified by one or more conventional operations, such as recrystallization, chromatography, and the like.

The aniline compound represented by formula (III) can be obtained in accordance via the following production route:

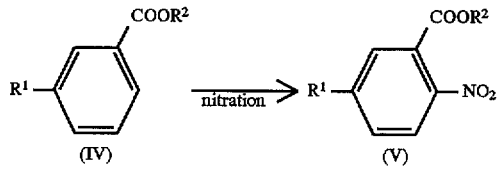

wherein:

$R^1$ represents a halogen; and $R^2$ represents a lower alkyl group.

An aniline compound containing chlorine as $R^1$ and methyl as $R^2$ can be obtained from Aldrich.

Compound (V) can then be reduced with, for example and without limitation, $H_2/PtO_2$ or $Fe/CH_3OOH$, to provide the aniline of formula (III).

The compound having a structure consistent with the aforementioned formula (I) also can be prepared by oxidizing a trifluoromethanesulfenanilide compound with a peroxidated compound, such as by way of example and without limitation, metachloroperbenzoic acid, magnesium monoperoxyphthalate, and the like.

The trifluoromethanesulfenanilide compound is represented by the following formula (VI):

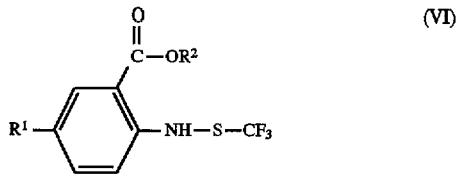

wherein:

$R^1$ represents a halogen; and $R^2$ represents a lower alkyl group.

The oxidizing reaction can be conducted in the presence of a solvent. Exemplary solvents that can be employed with metachlorobenzoic acid as the selected peroxidate compound include, without limitation, halogenated hydrocarbons, such as dichloromethane, chloroform, carbon tetrachloride, 1,2-dichloroethane, chlorobenzene, and the like, and any combination thereof. Where magnesium monoperoxyphthalate is selected as the peroxidate compound, exemplary solvents include, without limitation, alcohols, such as methanol, ethanol, and the like; water; and combinations thereof.

The reaction temperature for carrying out this reaction can be, for example, within a range from about −20° C. to about the boiling temperature of the selected solvent, or from about −20° C. to about 100° C.

The molar ratio of, one the one hand the trifluoromethanesulfenanilide compound with peroxidated compound, and on the other hand the selected base, is not limited and can be adjusted in accordance with routine experimentation. However, this ratio can advantageously be set to be equimolar or substantially equimolar.

Subsequent to completion of the reaction between the trifluoromethanesulfenanilide compound and the peroxidated compound, the reaction solution can be subjected to conventional post-treatment procedures, such as extraction with organic solvent, concentration and the like to isolate the resulting compound of formula (I). The compound then can be further purified by one or more conventional operations, such as recrystallization, chromatography, and the like.

The trifluoromethanesulfenanilide compound represented by formula (VI) can be produced, for example, by reacting the aniline compound represented by the above formula (III) with trifluoromethanesulfenyl chloride, generally having the molecular formula $CF_3SCl$, in the presence of a base. The trifluoromethanesulfenyl chloride can be prepared in accordance with the process described in J. Org. Chem., 25, 2016 (1960), the complete disclosure of which is incorporated herein by reference.

This reaction can be performed in the presence of a solvent. Exemplary solvents include, without limitation, the following: aliphatic hydrocarbons, such as n-hexane, n-heptane, and the like; alicyclic hydrocarbons, such as cyclohexane and the like; aromatic hydrocarbons, such as toluene, xylene, benzene, and the like; halogenated hydrocarbons, such as methylene chloride, chloroform, carbon tetrachloride, 1,2-dichloroethane, chlorobenzene, and the like; ethers, such as diisopropyl ether, tetrahydrofuran, dioxane, and the like; and any combination thereof.

Exemplary bases include, without limitation, the following: organic bases, such as pyridine, triethylamine, and the like; alkali metal hydroxides, such as sodium hydroxide, potassium hydroxide, and the like; alkali metal carbonates, such as sodium carbonate, potassium carbonate, and the like; and any combination thereof.

The reaction temperature for carrying out this reaction can be, for example, within a range from about −20° C. to about the boiling temperature of the selected solvent, or from about −20° C. to about 100° C.

The molar ratio of, one the one hand the aniline and trifluoromethanesulfenyl chloride, and on the other hand the selected base, is not limited and can be adjusted in accordance with routine experimentation. However, this ratio can advantageously be set to be equimolar or substantially equimolar.

Subsequent to completion of the reaction between the aniline and the trifluoromethanesulfenyl chloride, the reaction solution can be subjected to conventional post-treatment procedures, such as extraction with organic solvent, concentration and the like to isolate the desired trifluoromethanesulfenanilide compound having a structure in accordance with formula (VI). The trifluoromethanesulfenanilide compound then can be further purified by one or more conventional operations, such as recrystallization, chromatography, and the like.

The process for preparing trifluoromethanesulfonanilides from the trifluoromethanesulfinanilide compound having a structure set forth in formula (I) will now be described.

Exemplary magnesium monoperoxydicarboxylates that can be employed in this process include, without limitation, a magnesium salt of a compound having a carboxyl group and a peroxycarboxyl group (i.e., [—C(=O)OOH]) at the ortho position of a benzene ring, such as magnesium monoperoxyphthalate and the like; a magnesium salt of a compound having a carboxyl group and a peroxycarboxyl group at the vicinal position of an alicyclic hydrocarbon, such as magnesium monoperoxycyclohexane-1,2-dicarboxylate and the like; and magnesium monoperoxymaleate.

These magnesium monoperoxydicarboxylates are commercially available, or can be produced by the process set forth in EP-A-27693, the complete disclosure of which is incorporated herein by reference. The reaction can be conducted in a solvent. Exemplary solvents include the following: alcohols, such as methanol, ethanol, and the like; water; and a combination thereof.

The reaction temperature for carrying out this reaction can be, for example, within a range from about −20° C. to about the boiling temperature of the selected solvent, or from about −20° C. to about 100° C.

The molar ratio of magnesium monoperoxydicarboxylate to the trifluoromethanesulfinanilide compound having formula (I) can be in the range of from about 0.5:1 to about 2:1.

The reaction is preferably conducted in the presence of a base. Exemplary bases include, without limitation, carbonates of alkali metals, such as sodium carbonate, potassium carbonate, and the like; hydrogenated carbonates of alkali metals, such as sodium hydrogen carbonate, potassium hydrogen carbonate, and the like; hydroxides of alkali metals, such as sodium hydroxide, potassium hydroxide, and the like; and any combination thereof. The molar ratio of the base to magnesium monoperoxydicarboxylate can be in the range of from about 0.9:1 to about 1.2:1.

Subsequent to completion of the reaction between the magnesium monoperoxydicarboxylate and the trifluoromethanesulfinanilide compound having formula (I), the reaction solution can be subjected to conventional post-treatment procedures, such as extraction with organic solvent, concentration and the like to isolate the resulting trifluoromethanesulfonanilide of formula (II). The trifluoromethanesulfonanilide compound then can be further purified by one or more conventional operations, such as recrystallization, chromatography, and the like.

A trifluoromethanesulfinanilide compound, including mixtures of such compound, of the present invention also is suitable for use as an active ingredient of a controlling agent for regulating the population of house dust mites. Examples of such house dust mites include, without limitation, Dermatophagoides farinae Hughes and the like, and grain mites such as Tyrophagus putrescentiae and the like.

As the active ingredient of a controlling agent for house dust mites, in practice the trifluoromethanesulfinanilide compound of the present invention can be used alone or in combination with additional ingredients. Typically, the compound is supported by a solid carrier, a liquid carrier, a gaseous carrier, and/or bait, as required in accordance with the intended use of the agent. Further, a surfactant and other additives can be added to form the controlling agent, as required in accordance with the intended use of the agent.

Examples of formulations which the controlling agent can undertake include oil solutions, emulsifiable concentrates, wettable powders, flowables such as water suspensions and emulsions, granules, dusts, aerosols, heating fumigants such as combustible or chemical fumigants and porous ceramic fumigants, ULV agents, fog formulations (i.e., fogging agents), poison bait, and mite-controlling sheets.

These formulations can contain the trifluoromethanesulfinanilide compound as an active ingredient in an amount of, for example, about 0.01% by weight to about 95% by weight.

Exemplary solid carriers that can be employed in the formulation include, without limitation, fine powders or granules of clays (e.g., kaolin clay, diatomaceous earth, synthetic hydrated silicon dioxide, bentonite, Fubasami clay, acid clay, etc), talcs, ceramics, other inorganic minerals (e.g., sericite, quartz, sulfur, active carbon, calcium carbonate, hydrated silica, etc.), and chemical fertilizers (e.g., ammonium sulfate, ammonium phosphate, ammonium nitrate, urea, ammonium chloride, etc.). Exemplary liquid carriers include, without limitation, water, alcohols (e.g., methanol, ethanol, etc.), ketones (e.g., acetone, methyl ethyl ketone, etc.), aromatic hydrocarbons (e.g., benzene, toluene, xylene, ethylbenzene, methylnapthalene, etc.), aliphatic hydrocarbons (e.g., hexane, cyclohexane, kerosine, gas oil, etc.), esters (e.g., ethyl acetate, butyl acetate, etc.), nitriles (e.g., acetonitrile, isobutyronitrile, etc.), ethers, (e.g., diisopropyl ether, dioxane, etc.), acid amides (e.g., N,N-dimethylforamide, N,N-dimethylacetamide, etc.), halogenated hydrocarbons (e.g., dichloromethane, trichloroethane, carbon tetrachloride, etc.), dimethyl sulfoxide, and vegetable oils (e.g., soybean oil, cottonseed oil, etc.). Exemplary gaseous carriers or propellants include, without limitation, CFCs (chlorofluorocarbons), butane gas, LPG (liquefied petroleum gas), dimethyl ether, carbon dioxide, and the like.

Exemplary surfactants include, without limitation, alkyl sulfates, alkyl sulfonates, alkyl aryl sulfonates, alkyl aryl ethers and polyoxyethylenates thereof, polyethylene glycol ethers, polyhydric alcohol esters, and sugar alcohol derivatives and the like.

Exemplary adjuvants for formulations such as stocking agents, dispersing agents and the like include, without limitation, casein, gelatin, polysaccharides (e.g., starch, gum arabic, cellulose derivatives, alginic acid, etc), lignin derivatives, bentonite, sugars, and synthetic water-soluble polymers (e.g., polyvinyl alcohol, polyvinyl pyrrolidone, polyacrylic acids, etc). Exemplary stabilizers include, without limitation, PAP (acid isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids, and esters of fatty acids.

Exemplary base materials of the combustible fumigant include, without limitation, the following: exothermic agents, such as nitrates, nitrites, guanidine salt, potassium chlorate, nitrocellulose, ethylcellulose, wood powder and the like; pyrolytic stimulating agents, such as alkali metal salts, alkaline earth metal salts, dichromates, chromates and the like; oxygen sources, such as potassium nitrate and the like; combustion assistants, such as melamine, wheat starch and the like; bulk fillers such as diatomaceous earth and the like; and binding agents, such as synthetic glue and the like.

Exemplary base materials of the chemical fumigant include without limitation, the following: exothermic agents, such as sulfides, polysulfides, hydrosulfides and water-containing salts of alkaline metal, and the like; catalytic agents, such as carbonaceous substances, iron carbide, active clay and the like; organic foaming agents such as azodicarbonamide, benzenesulfonylhydrazine, dinitrosopentamethylenetetramine, polystyrene, polyurethane and the like; and fillers such as natural fibers, synthetic fibers and the like.

Exemplary base materials of the poisonous bait include, without limitation, the following: bait materials, such as grain powder, vegetable oil, sugar, crystalline cellulose and the like; antioxidants, such as dibutylhydroxytoluene, nordihydroguaiaretic acid and the like; preservatives such as dehydroacetic acid and the like; substances for preventing erroneous eating such as red pepper powder and the like; and attractants such as cheese flavor, onion flavor, peanut oil and the like.

The formulations thus obtained can be used alone or can be diluted with water, and can be used simultaneous with other insecticides, acaricides or synergists under non-mixed conditions or pre-mixed conditions.

Examples of the insecticides and/or acaricides include, without limitation, the following: organophosphorus compounds, such as Fenitrothion, Fention, Diazinon, Chlorpyriphos, Acephate, Methidachion, Disulfoton, DDVP, Sulprofos, Cyanophos, Dioxabenzofos, Dimethoate, Phenthoate, Malathion, Trichlorfon, Azinphosmethyl, Monocrotophos, Ethion and the like; carbamate compounds, such as BPMC, Benfuracarb, Propoxur, Carbaril, Ethiofencarb. Aldicarb, Oxamyl and the like; pyrethroid compounds, such as Etofenprox, Fenvalerate, es-Fenvalerate, Fenpropathrin, Cypermethrin, Permethrin, Cyhalothrin, Deltamethrin, Cycloprothrin, d-Phenothrin, Tetramethrin, d-Allethrin, Resmethrin, Phthalthrin, Empenthrin, Prallelthrin, Fluvalinate, Bifenthrin, Acrinathrin, Traromethrin, Silafluofen and the like; thiadiazine derivatives, such as Buprofezin and the like; nitroimidazolidine derivatives, such as Imidacloprid and the like; Nereistoxin derivatives, such as Cartap and the like; benzolyphenylurea compounds, such as Teflubenzuron, Fulphenoxron and the like; thiourea derivatives, such as Diafenthiuron and the like; Debphenizide; 4-bromo-2-(4-chlorophenyl)-1-ethoxyethyl-5-trifluoromethylpyrrole-3-carbonitrile; phenyl salicylate; benzyl benzoate, paraoxybenzoate; formal iodide; phenols; phthalate; Methoxadiazon; and monoterpene epoxides.

When the present compound is applied as an active ingredient of the control agent for house dust mites, emulsifiable concentrates, wettable powders and flowables are usually diluted with water to provide a concentration in a range of about 0.01 ppm to about 10,000 ppm (i.e., parts of active ingredient per million parts of control agent). Oil solutions, aerosols, fumigants, fogging agents, ULV agents, poisonous baits and mite-controlling sheets can be applied as prepared without further modifications.

The amount and concentration of the active ingredient employed in application can be varied optionally according to the type of the formulation, timing, place, method of application, the type of house dust mites, and the population of house dust mites.

A trifluoromethanesulfinanilide compound, a process relating to the preparation of trifluoromethanesulfonanilide from the same, and a controlling agent containing trifluoromethanesulfinanilide as an active ingredient are disclosed in (a) Application No. 07-318850, filed on Dec. 7, 1995 in Japan; (b) Application No. 08-176266 filed on Jul. 5, 1996 in Japan; and (c) Application No. 08-239592 filed on Sep. 10, 1996 in Japan. The complete disclosures of each application (a), (b), and (c) are incorporated herein by reference.

EXAMPLES

The following examples serve to further illustrate the present invention in detail but are not to be construed to limit the scope of the invention.

Production Examples of the present invention are described hereinafter.

Production Example 1

To a solution containing 2-methoxycarbonyl-4-chloro-trifluoromethanesulfenanilide (also referred to as 1,1,1-trifluoro-N-[4-chloro-2-(methoxycarbonyl)phenyl] methanesulfenamide) (produced in Reference Production Example 1 described hereinafter) (0.50 g, 1.8 mmol) in a dried dichloromethane (10 ml) solvent was added metachloroperbenzoic acid (manufactured by Wako Junyaku Co., Ltd., purity: 70%) (0.47 g, 1.9 mmol) under ice cooling. After stirring at room temperature for 12 hours, the reaction solution was poured into ice water to obtain the dichloromethane layer. The aqueous layer was extracted once with dichloromethane, and the resulting dichloromethane layer was combined with the above dichloromethane layer. The combined layer was washed in turn with a saturated sodium thiosulfate solution and a saturated sodium hydrogen carbonate solution and dried over anhydrous magnesium sulfate, and then the solvent was distilled off under reduced pressure. The resultant residue was subjected to silica gel chromatography to obtain 0.17 g of 2-methoxycarbonyl-4-chloro-trifluoromethanesulfinanilide (also referred to as 1,1,1-trifluoro-N-[4-chloro-2-(methoxycarnbonyl)phenyl]methanesulfinamide] (present compound (1)) (0.56 mmol, yield: 32%).

$^1$H-NMR (CDCl$_3$/TMS, δ (ppm)):4.0 (3H, s), 7.3 (1H, d), 7.5 (1H, dd), 8.0 (1H, d), 10.5 (1H, brs) m.p, 65.9° C.

Production Example 2

To a mixture of methyl 5-chloro-2-aminobenzoate (0.66 g, 3.6 mmol) and triethylamine (0.39 g, 3.9 mmol) in a dried chloroform solvent (10 ml) was added trifluoromethanesulfinyl chloride (0.60 g, 3.9 mmol) under ice cooling. [The trifluoromethanesulfinyl chloride was prepared as follows: To a mixture of potassium sulfite (19.3 g) and water (40 ml) was added dropwise trifluoromethanesulfonyl chloride (5.2 g) under ice cooling. After stirring at room temperature for 2 hours, the reaction solution was filtered. The residue obtained by concentrating the filtrate was extracted twice with heated acetone and the extracted solution was concentrated. The solid obtained by sufficiently drying the residue was heated at reflux, together with thionyl chloride (40 ml), for 2 hours. The reaction mixture was distilled under a normal pressure to obtain 1.3 g of trifluoromethanesulfinyl chloride.] After stirring at room temperature for one hour, the reaction solution was poured into ice water to obtain the chloroform layer. The aqueous layer was extracted once with chloroform and the obtained chloroform layer was combined with the above chloroform layer. The combined layer was washed in turn with water and a saturated sodium chloride solution and dried over anhydrous magnesium sulfate. Then the solvent was distilled off under reduced pressure. The resultant residue was subjected to silica gel chromatography to obtain 0.64 g of 2-methoxycarbonyl-4-chloro-trifluoromethanesulfinanilide (also referred to as 1,1,1,-trifluoro-N-[4-chloro-2-(methoxycarbonyl)phenyl]methanesulfinamide) (present compound (1)) (2.1 mmol, yield: 60%).

Production Example 3

To a mixture of methyl 5-chloro-2-aminobenzoate (0.93 g, 5.0 mmol) and triethylamine (0.56 g, 5.5 mmol) in a dried chloroform solvent (15 ml) was added trifluoromethanesulfinyl chloride (0.84 g, 5.5 mmol) under ice cooling. [The trifluloromethanesulfinyl chloride was prepared as follows: sodium trifluoromethanesulfinate (31.2 g, 200 mmol) and thionyl chloride (47.6 g, 400 mmol) were mixed under ice cooling, followed by stirring at room temperature for 2 hours. The reaction mixture was distilled (b.p. 40°–43° C.) under a normal pressure to obtain 12 g of trifluoromethanesulfinyl chloride.] After stirring at room temperature for one hour, the reaction solution was poured into ice water to obtain the chloroform layer. The aqueous layer was extracted once with chloroform and the thus obtained chloroform layer was combined with the above chloroform layer. The combined layer was washed in turn with water and a saturated sodium chloride solution and dried over anhydrous magnesium sulfate, and then the solvent was distilled off under reduced pressure. The resultant resident was subjected to silica gel chromatography to obtain 0.94 g of 2-methoxycarbonyl-4-chloro-trifluoromethanesulfinanilide (also referred to as 1,1,1-trifluoro-N-[4-chloro-2-(methoxycarbonyl)phenyl]methanesulfinamide) (present compound (1)) (3.1 mmol, yield: 62%).

Production Example 4

To a mixture of methyl 5-chloro-2-aminobenzoate (0.93 g, 5.0 mmol) and N,N-diethylaniline (0.82 g, 5.5 mmol) in a dried toluene solvent (15 ml) was added trifluoromethanesulfinyl chloride (0.84 g, 5.5 mmol) [the compound was prepared according to the process described in Production Example 3] under ice cooling. After stirring at room temperature for 3 hours, the reaction solution was poured into ice water to obtain the toluene layer. The aqueous layer was extracted once with toluene and the thus obtained toluene layer was combined with the above toluene layer. The combined layer was washed in turn with water and a saturated sodium chloride solution and dried over anhydrous magnesium sulfate, and then the solvent was distilled off under reduced pressure. The resultant residue was subjected to silica gel chromatography to obtain 1.29 g of 2-methoxycarbonyl-4-chloro-trifluoromethanesulfinanilide (also referred to as 1,1,1-trifluoro-N-[4-chloro-2-(methoxycarbonyl)phenyl]-methanesulfinamide) (present compound (1)) (4.3 mmol, yield: 85%).

Production Example 5

To a mixture of methyl 5-chloro-2-aminobenzoate (0.93 g, 5.0 mmol), pyridine hydrochloride (0.58 g, 5.0 mmol), sodium trifluoromethanesulfinate (0.78 g, 5.0 mmol) and dried toluene (15 ml) was added thionyl chloride (0.60 g, 5.0 mmol), under ice cooling. After stirring at room temperature for 2 hours, the reaction solution was analyzed by gas chromatography [analysis conditions were as follows:

(i) column: 10% DEXSIL 300GC (manufactured by Shimadzu Corp.);
(ii) column temperature: 170° C.;
(iii) injection temperature: 200° C.;
(iv) carrier gas: nitrogen gas;
(v) flow rate of carrier gas: 50 ml/minute; and
(vi) detection: FID].

The desired 2-methoxycarbonyl-4-chloro-trifluoromethanesulfinanilide was formed in a peak area percentage of gas chromatogram (hereinafter referred to as "the area percentage") of 80%.

Other compounds of the present invention which can be produced according to the above Production Examples 1 to 5 having a structure in accordance with formula (I), and the corresponding numbers assigned to these compounds hereinafter, are as follows:

(2) 2-Methoxycarbonyl-4-bromo-trifluoromethanesulfinanilide
(3) 2-Ethoxycarbonyl-4-chloro-trifluoromethanesulfinanilide.

An example of a procedure for producing the trifluoromethanesulfenanilide compound represented by the formula (VI) is described hereinafter.

Reference Production Example 1

To a mixture of methyl-5-chloro-2-aminobenzoate (0.98 g, 5.3 mmol) and triethylamine (0.59 g, 5.8 mmol) in a dried chloroform solvent (10 ml) was added trifluoromethanesulfenyl chloride (0.79 g, 5.8 mmol) under ice cooling. [The trifluoromethanesulfenyl chloride was prepared as follows: To a mixture of trichloromethanesulfenyl chloride (9.3 g, 50 mmol) and dried sulfolane (40 ml) was added potassium fluoride (6.2 g, 100 mmol). While the reaction solution was heated to 50° to 200° C., trifluoromethanesulfenyl chloride formed was cooled and obtained (2.1 g) by dry ice-acetone trap.] After stirring at room temperature for one hour, the reaction solution was poured into ice water to obtain the chloroform layer. The aqueous layer was extracted once with chloroform and the thus obtained chloroform layer was combined with the above chloroform layer. The combined layer was washed in turn with water and a saturated sodium chloride solution and dried over anhydrous magnesium sulfate, and then the solvent was distilled off under reduced pressure. The resultant residue was subjected to silica gel chromatography to obtain 0.60 g of 2-methoxycarbonyl-4-chloro-trifluoromethanesulfenanilide (also referred to as 1,1, 1-trifluoro-N-[4-chloro-2-(methoxycarbonyl)phenyl] methanesulfenamide) (2.1 mmol, yield: 40%).

$^1$H-NMR (CDCl$_3$/TMS, δ(ppm)): 3.9 (3H, s), 7.4 (1H, dd), 7.5 (1H, d), 7.9 (1H, d), 9.0 (1H, brs) $n_D^{25.0}$1.5297.

Examples of the present process are described hereinafter.

Example 1

To a solution containing the present compound (1) (0.50 g, 1.7 mmol) in a methanol solvent (10 ml) was added magnesium monoperoxyphthalate haxahydrate (manufactured by Tokyo Kasei Kogyo Co., Ltd., purity: 95%) (0.86 g, 1.7 mmol) while stirring. After stirring at room temperature for 6 hours, the reaction solution was poured into ice water. The aqueous layer was extracted twice with chloroform and the chloroform layers were combined. The combined layer was dried over anhydrous magnesium sulfate, and then the solvent was distilled off under reduced pressure. The resultant residue was subjected to silica gel chromatography to obtain 0.26 g of 2-methoxycarbonyl-4-chloro-trifluoromethanesulfonanilide (also referred to as 1,1, 1-trifluoro-N-[4-chloro-2-(methoxycarbonyl)phenyl] methanesulfonamide) (0.82 mmol, yield: 49%).

$^1$H-NMR (CDCl$_3$/TMS, δ (ppm)): 4.0 (3H, s), 7.5 (1H, dd), 7.7 (1H, d), 8.1 (1H, d), 11.0 (1H, brs).

Example 2

To a solution containing the present compound (1) (0.50 g, 1.7 mmol) in a methanol solvent (10 ml) were added magnesium monoperoxyphthalate haxahydrate (manufactured by Tokyo Kasei Kogyo Co., Ltd., purity: 95%) (0.86 g, 1.7 mmol) and sodium carbonate (0.18 g, 1.7 mmol) while stirring. After stirring at room temperature for 6 hours, the reaction solution was analyzed by gas chromatography [analysis conditions were as follows (which are the same in the following Examples):
(i) column: 10% DEXSIL 300GC (manufactured by Shimadzu Corp.);
(ii) column temperature: 170° C.;
(iii) injection temperature: 200° C.;
(iv) carrier gas: nitrogen gas;
(v) flow rate of carrier gas: 50 ml/minute; and
(vi) detection: FID].

After confirming that the desired 2-methoxycarbonyl-4-chloro-trifluoromethanesulfonanilide was formed in a peak area percentage of gas chromatogram (hereinafter referred to as "the area percentage") of 91%, the reaction solution was poured into ice water. The aqueous layer was extracted twice with chloroform and the chloroform layers were combined. The combined layer was dried over anhydrous magnesium sulfate, and then the solvent was distilled off under reduced pressure. The resultant residue was subjected to silica gel chromatography to obtain 0.44 g of 2-methoxycarbonyl-4-chloro-trifluoromethane-sulfonanilide (1.4 mmol, yield: 84%).

Example 3

To a solution containing the present compound (1) (0.50 g, 1.7 mmol) in a solvent of methanol (7.5 ml) and water (2.5 ml) were added magnesium monoperoxyphthalate haxahydrate (manufactured by Tokyo Kasei Kogyo Co., Ltd., purity: 95%) (0.86 g, 1.7 mmol) and sodium carbonate (0.18 g, 1.7 mmol) while stirring. After stirring at room temperature for 6 hours, the reaction solution was analyzed by gas chromatography to confirm that the desired 2-methoxycarbonyl-4-chloro-trifluoromethanesulfonanilide was formed in the area percentage of 82%.

Example 4

To a solvent containing the present compound (1) (0.50 g, 1.7 mmol) in a methanol solvent (10 ml) were added magnesium monoperoxyphthalate haxahydrate (manufactured by Tokyo Kasei Kogyo Co., Ltd., purity: 95%) (0.86 g, 1.7 mmol) and sodium hydrogen carbonate (0.14 g, 1.7 mmol) while stirring. After stirring at room temperature for 6 hours, the reaction solution was analyzed by gas chromatography to confirm that the desired 2-methoxycarbonyl-4-chloro-trifluoromethanesulfonanilide was formed in the area percentage of 74%.

Example 5

To a solution containing the present compound (1) (0.50 g, 1.7 mmol) in a methanol solvent (10 ml) were added magnesium monoperoxyphthalate haxahydrate (manufactured by Tokyo Kasei Kogyo Co., Ltd., purity: 95%) (0.86 g, 1.7 mmol) and sodium hydroxide (0.066 g, 1.7 mmol) while stirring. After stirring at room temperature for 6 hours, the reaction solution was analyzed by gas chromatography to confirm that the desired 2-methoxycarbonyl-4-chloro-trifluoromethanesulfonanilide was formed in the area percentage of 64%.

Other trifluoromethanesulfonanilide compounds having the formula (II) which can be produced according to the above Examples, are 2-methoxycarbonyl-4-bromo-trifluoromethanesulfonanilide and 2-ethoxycarbonyl-4-chloro-trifluoromethanesulfonanilide.

An embodiment wherein metachloroperbenzoic acid was used in place of magnesium monoperoxyphthalate in the process of the present invention is described hereinafter.

Comparative Example 1

To a mixture of the present compound (1) (0.50 g, 1.7 mmol) and dried dichloromethane solvent (10 ml) was added metachloroperbenzoic acid (manufactured by wako junyaku Co., Ltd., purity: 70%) (0.45 g, 1.8 mmol) while stirring under ice cooling. After stirring at room temperature for 20 hours, the reaction solution was poured into ice water to obtain the dichloromethane layer. The aqueous layer was extracted once with dichloromethane and the thus obtained dichloromethane layer was combined with the above dichloromethane layer. The combined layer was washed in turn with a saturated sodium thiosulfate solution and a saturated sodium hydrogen carbonate solution and then dried over anhydrous magnesium sulfate, and then the solvent was distilled off under reduced pressure. The resultant residue was subjected to silica gel chromatography to obtain 0.16 g of 2-methoxycarbonyl-4-chlorotrifluoromethanesulfonanilide (also referred to as 1,1,1-trifluoro-N-[4-chloro-2-(methoxycarbonyl) phenyl] methanesulfonamide) (0.50 mmol, yield: 30%).

Formulation Examples are described hereinafter. In the description below, the present compounds are designated by their corresponding numbers as mentioned above and parts are represented in parts by weight.

Formulation Example 1

Emulsifiable concentrates

For each of the present compounds (1) to (3), 10 parts of the present compound (1), (2), or (3) were dissolved in 35 parts of xylene and 35 parts of dimethylformamide. Each of the obtained mixtures was mixed with 14 parts of polyoxyethylene styrylphenyl ether and 6 parts of calcium dodecylbenzenesulfonate, and stirred sufficiently to give a 10% emulsifiable concentrate for each compound.

Formulation Example 2

Wettable powders

For each of the present compounds (1) to (3), 20 parts of the present compound (1), (2), or (3) were added to a mixture of 4 parts of sodium laurylsulfate, 2 parts of calcium lignin sulfonate, 20 parts of synthetic hydrated silicon dioxide fine powder and 54 parts of diatomaceous earth, and the mixture was pulverized and mixed with a juice mixer to give 20% wettable powder for each compound.

Formulation Example 3

Granules

For each of the present compounds (1) to (3), 5% granules of the present compound (1), (2), or (3) were obtained by sufficiently mixing 5 parts of sodium dodecylbenzenesulfonate, 30 parts of bentonite and 60 parts of clay with the present compound (1), (2), or (3), respectively, kneading with an appropriate amount of water, granulating the mixture with a granulator, and thereafter air drying.

Formulation Example 4

Dusts

For each of the present compounds (1) to (3), 1 part of the present compound (1), (2), or (3) was dissolved in an appropriate amount of acetone and mixed with 5 parts of synthetic hydrated silicon dioxide fine powder, 0.3 part of PAP and 93.7 parts of clay, and the mixture was pulverized and mixed in a juice mixer to give 1% dusts for each compound.

Formulation Example 5

Flowables

For each of the present compounds (1) to (3), 10 parts of the compound (1), (2), or (3) were mixed with 40 parts of an aqueous solution containing 6 parts of polyvinyl alcohol, and the mixture was wet-pulverized to give a suspension. Ten percent flowables for each compound were obtained by mixing the suspension with 40 parts of an aqueous solution containing 0.05 part of xantan gum and 0.1 part of aluminum magnesium silicate and then 10 parts of propylene glycol while stirring mildly.

Formulation Example 6

Oil solutions

For each of the present compounds (1) to (3), a 0.1% oil solution was obtained by dissolving 0.1 part of the present compound (1), (2), or (3), respectively, in 5 parts of xylene and 5 parts of trichloroethane, and mixing the solution with 89.9 parts of deodorized kerosine.

Formulation Example 7

Oil-based aerosol

For each of the compounds (1) to (3), 0.1 part of the compound (1), (2) or (3), 0.2 part of tetramethrin, 0.1 part of d-phenothrin and 10 parts of trichloroethane in 59.6 parts of deodorized kerosine were mixed and the mixture was filled in an aerosol vessel. Then the vessel was set up with a valve, through which 30 parts of a propellant (liquefied petroleum gas) were charged under pressure to give each oil-based aerosol.

Formulation Example 8

Water-based aerosol

For each of the compounds (1) to (3), 0.2 part of the compound (1), (2), or (3), 0.2 part of d-allethrin, 0.2 part of d-phenothrin, 5 parts of xylene, 3.4 parts of deodorized kerosine, and 1 part of an emulsifier [Atmos 300 (registered trade mark by Atlas Chemical)] were mixed, and the mixture and 50 parts of pure water were filled in an aerosol vessel. Then the vessel was equipped with a valve, through which 40 parts of a propellant (liquefied petroleum gas) were charged under pressure.

Formulation Example 9

Bait

Separate solutions prepared by dissolving 10 mg of each of the present compounds (1) to (3) separately in 0.5 ml of acetone were respectively mixed homogeneously with 5 g of solid bait powder for animals (Breeding Solid Feed Powder CE-2: trade name by Clea Japan Corp.). The acetone was removed by air-drying to obtain 0.5% poison bait for each compound.

Formulation Example 10

Volatile agent

A volatile agent was prepared for each of the present compounds (1) to (3) by applying a solution prepared by separately dissolving 500 µg of each of the present compounds (1) to (3) in an appropriate amount of acetone onto filter paper (2 cm×2 cm, 0.3 mm in thickness), and removing the acetone by air-drying.

Formulation Example 11

Mite-controlling sheet

For each of the present compounds (1) to (3), a solution of the compound (1), (2), or (3) in acetone was added dropwise to filter paper so that a concentration of each compound was 1 g/lm$^2$ after being air-dried to remove the acetone to give mite-controlling sheet of each compound.

Formulation Example 12

Heating fumigant

Heating fumigants, each containing one of the present compounds (1) to (3), were prepared by impregnating a porous ceramic plate (4.0 cm×4.0 cm, 1.2 cm in thickness) with solutions prepared by dissolving 100 mg of the present compound (1), (2), or (3), respectively, in an appropriate amount of acetone.

The following test example was performed to demonstrate that the present compound is useful as an active ingredient of a control agent of house dust mites. In the description below, the present compounds are designated by their corresponding numbers as set forth above.

Test Example 1

Test against mites (Tyrophagus putrescentiae and Dermatophagoides farinae Huges)

A piece of filter paper (diameter: 4 cm) was impregnated uniformly with an acetone solution of the present compound so that the amount of the impregnated compound was 0.8 g/m² after being air-dried. Approximately twenty heads of mites (Tyrophagus putrescentiae or Dermatophagoides farinae Huges) were put on the surface of the filter paper. An adhesive substance was applied on the circumference of the filter paper for preventing escape. After one day, the mortality was examined.

As a result, the present compound (1) showed the mortality of 100% against Tyrophagus putrescentiae and Dermatophagoides farinae Huges, respectively. In the non-treated filter paper, the mortalities against Tyrophagus putrescentiae and Dermatophagoides farinae Huges were each 0%.

Although the present invention has been described in detail with reference to its presently preferred embodiments, it will be understood by those of ordinary skill in the art that various modifications and improvements to the present invention are believed to be apparent to one skilled in the art. All such modifications and improvements are intended to be included within the scope of the following appended claims.

What is claimed is:

1. A trifluoromethanesulfinanilide compound having the formula

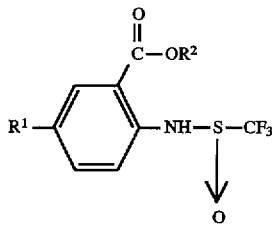

wherein $R^1$ is a halogen atom, and $R^2$ is a lower alkyl group.

2. A trifluoromethanesulfinanilide compound according to claim 1, wherein $R^1$ is selected from the group consisting of a bromine atom and a chlorine atom.

3. A trifluoromethanesulfinanilide compound according to claim 1, wherein $R^2$ is selected from the group consisting of a methyl, ethyl, propyl, and butyl group.

4. A trifluoromethanesulfinanilide compound according to claim 1, wherein said compound is 2-methoxycarbonyl-4-chloro-trifluoromethanesulfinanilide.

5. A trifluoromethanesulfinanilide compound according to claim 1, wherein said compound is 2-methoxycarbonyl-4-bromo-trifluoromethanesulfinanilide.

6. A trifluoromethanesulfinanilide compound according to claim 1, wherein said compound is 2-ethoxycarbonyl-4-chloro-trifluoromethanesulfinanilide.

7. A process for preparing a trifluoromethanesulfonanilide having the following formula

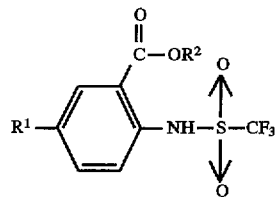

wherein $R^1$ is a halogen atom, and $R^2$ is a lower alkyl group, said process comprising oxidizing a trifluoromethanesulfinanilide compound (I) with a magnesium monoperoxydicarboxylate, said trifluoromethanesulfinanilide compound (I) having the following formula

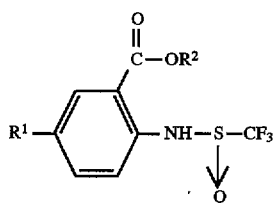

wherein $R^1$ is a halogen atom, and $R^2$ is a lower alkyl group.

8. A process according to claim 7, further comprising providing a base, wherein said oxidizing step is conducted in the presence of said base.

9. A process according to claim 8, wherein said base is at least one member selected from the group consisting of an alkali carbonate, an alkali hydrogen carbonate, and an alkali hydroxide.

10. A process according to claim 8, wherein said base is an alkali carbonate.

11. A process according to claim 10, wherein said base is sodium carbonate.

12. A process according to claim 7, wherein said magnesium monoperoxydicarboxylate is magnesium monoperoxyphthalate.

13. A process according to claim 8, wherein said magnesium monoperoxydicarboxylate is magnesium monoperoxyphthalate.

14. A process according to claim 9, wherein said magnesium monoperoxydicarboxylate is magnesium monoperoxyphthalate.

15. A process according to claim 10, wherein said magnesium monoperoxydicarboxylate is magnesium monoperoxyphthalate.

16. A process according to claim 11, wherein said magnesium monoperoxydicarboxylate is magnesium monoperoxyphthalate.

17. A controlling agent for regulating the population of house dust mites or grain mites, comprising an insecticidally effective amount of an active agent comprising a trifluoromethanesulfinanilide compound having the formula

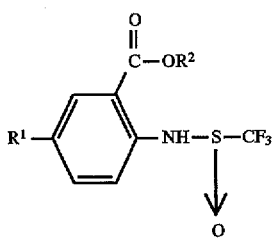

(I)

wherein $R^1$ is a halogen atom, and $R^2$ is a lower alkyl group.

18. A process of controlling the population of house dust mites or gain mites, comprising applying a controlling agent to house dust mites or grain mites or a locus where house dust mites or grain mites inhabit, said controlling agent comprising an insecticidally effective amount of an active agent comprising a trifluoromethanesulfinanilide compound having the formula

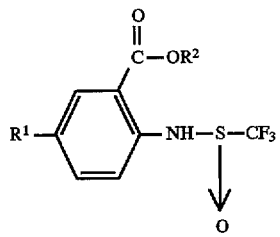

(I)

wherein $R^1$ is a halogen atom, and $R^2$ is a lower alkyl group.

* * * * *